United States Patent [19]

Transue

[11] Patent Number: 5,562,611

[45] Date of Patent: Oct. 8, 1996

[54] SAFETY INTERPOSER FOR SURGICAL INSTRUMENTS

[75] Inventor: Deborah M. Transue, Bridgewater, N.J.

[73] Assignee: Ethicon Endo-Surgery, Inc., Cincinnati, Ohio

[21] Appl. No.: 304,957

[22] Filed: Sep. 13, 1994

Related U.S. Application Data

[63] Continuation-in-part of Ser. No. 61,973, May 17, 1993, abandoned.

[51] Int. Cl.$^6$ ................................................. A61B 17/34
[52] U.S. Cl. ........................... 604/26; 604/170; 604/158; 606/185
[58] Field of Search ........................... 604/26, 170, 158; 606/185

[56] References Cited

U.S. PATENT DOCUMENTS

| | | | |
|---|---|---|---|
| 4,869,717 | 9/1989 | Adair | 604/26 X |
| 5,030,206 | 7/1991 | Lander | 604/164 |
| 5,114,407 | 5/1992 | Burbank | 604/164 |
| 5,261,891 | 11/1993 | Brinkerhoff et al. | 604/170 X |
| 5,364,372 | 11/1994 | Danks et al. | 604/26 X |

FOREIGN PATENT DOCUMENTS

| | | | |
|---|---|---|---|
| 0537498A2 | 4/1993 | European Pat. Off. | A61B 17/072 |
| 9101109 U | 1/1991 | Germany | A61B 17/34 |

*Primary Examiner*—Michael H. Thaler

[57] ABSTRACT

Packaging for use in transportation and handling of a surgical instrument including a safety device which prevents engagement of the instrument or movement of a safety mechanism from a safety position. In a preferred embodiment the safety device is a safety interposer shaped to fit into a slot in the shaft of a Veress-type needle. The safety interposer acts as a physical barrier to prevent the movement of an inner needle with respect to an outer needle, thereby preventing exposure of the sharp edges of the outer needle particularly during transportation or handling.

2 Claims, 6 Drawing Sheets

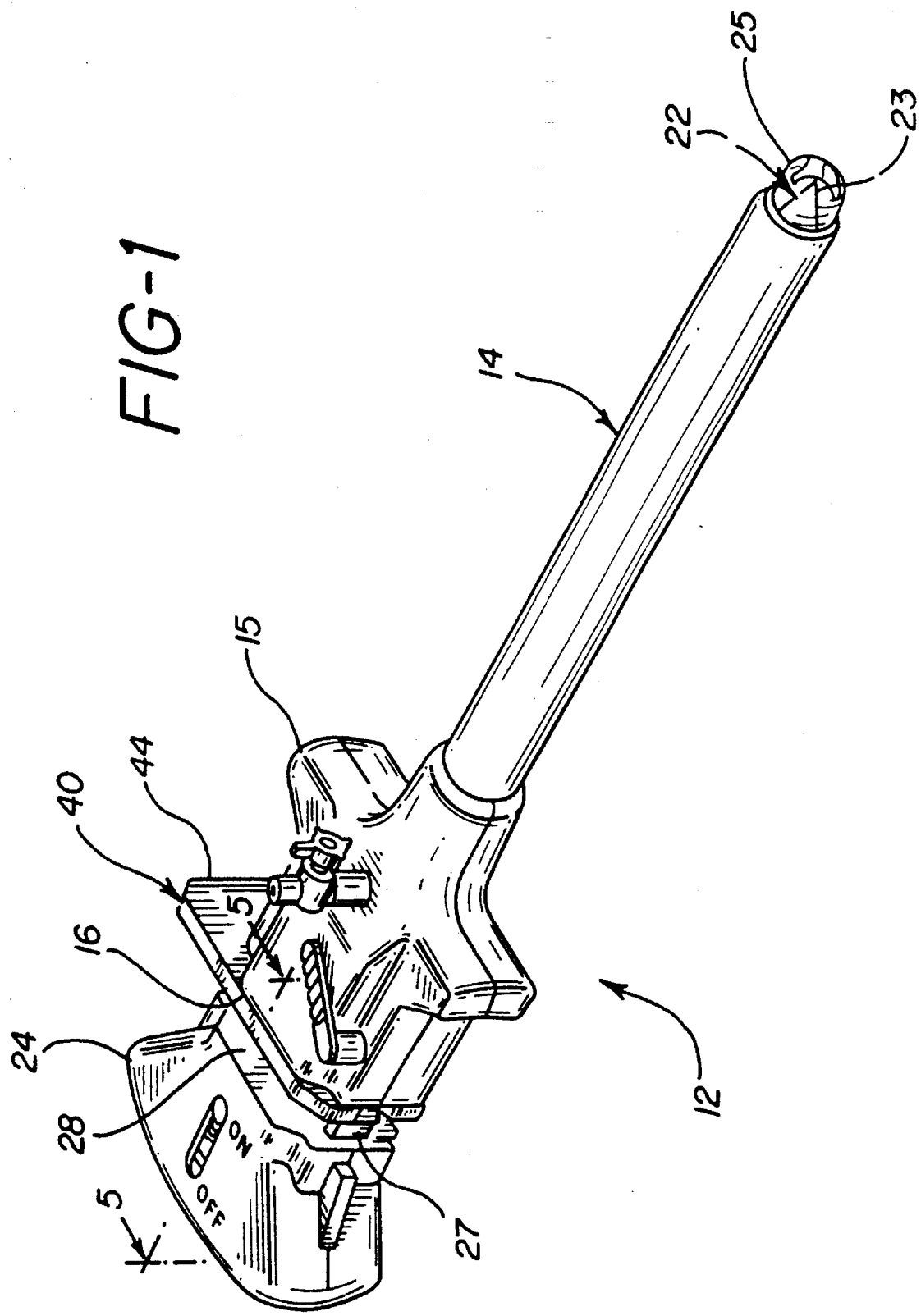

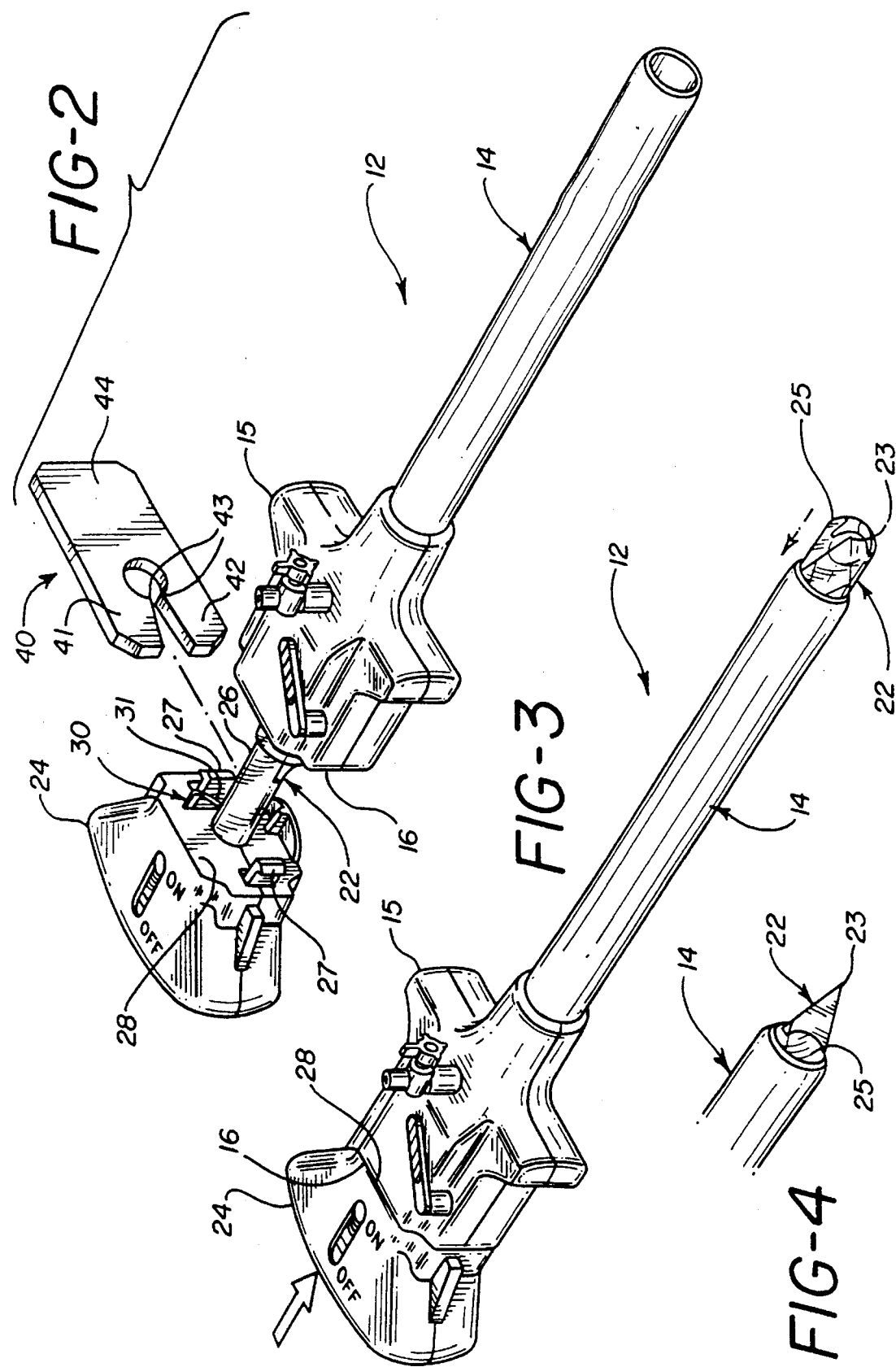

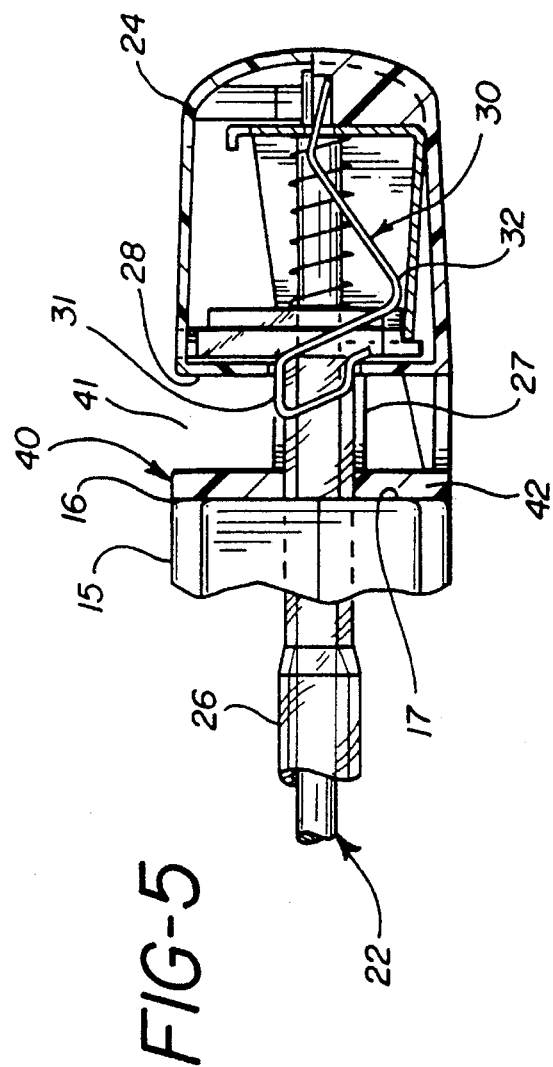
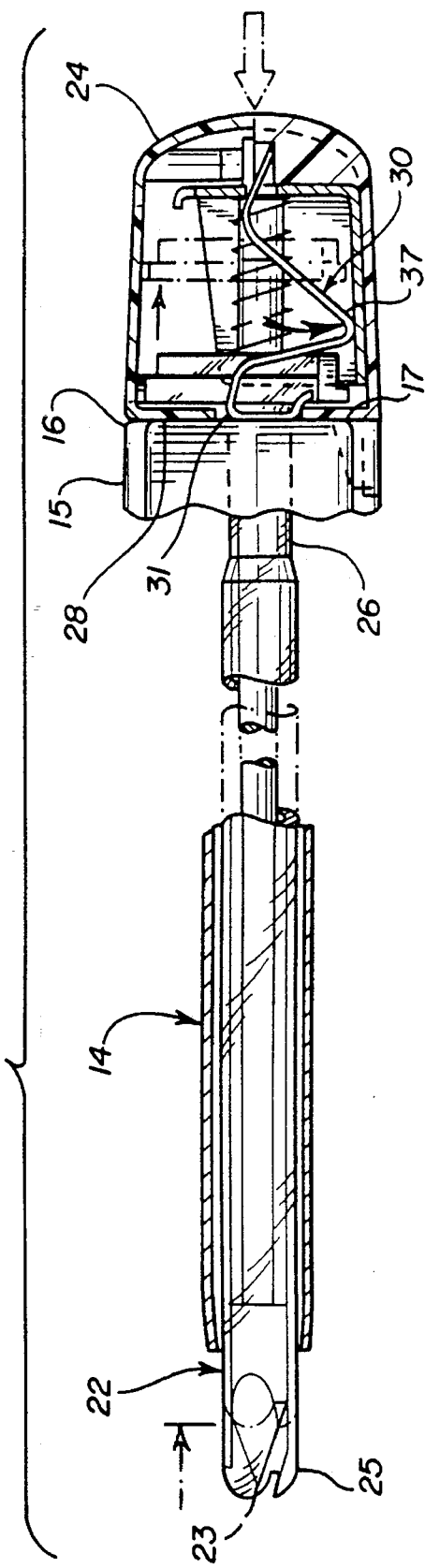

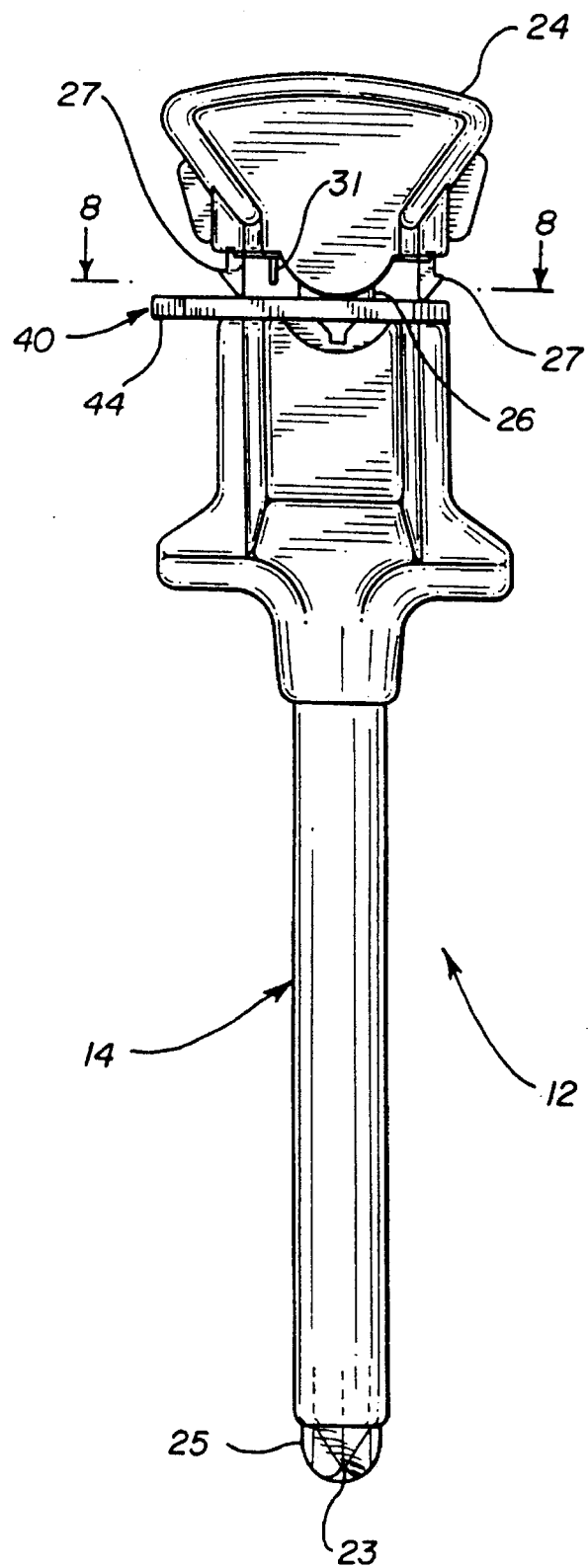
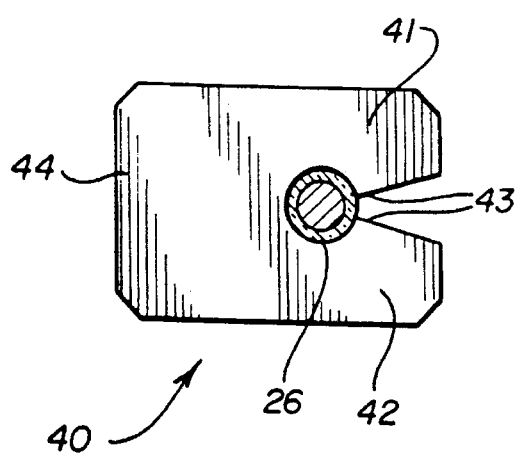
FIG-7
FIG-8

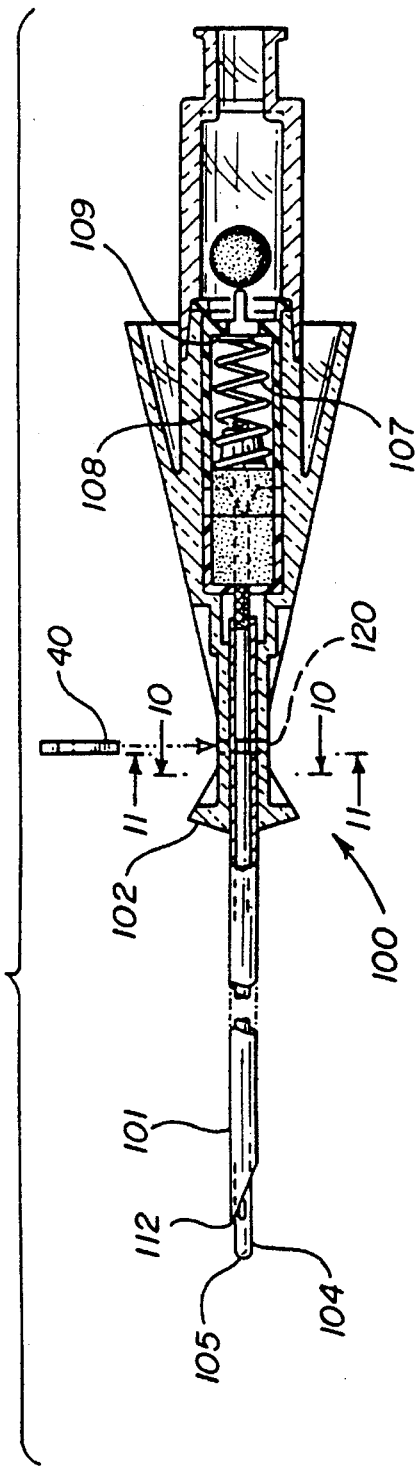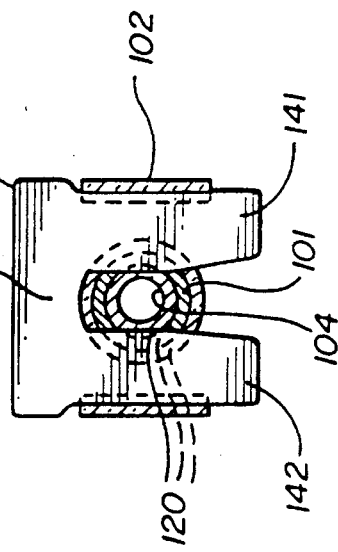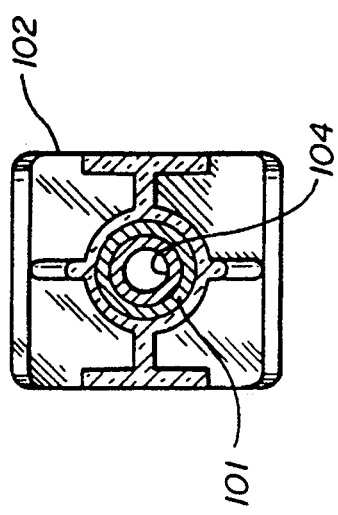

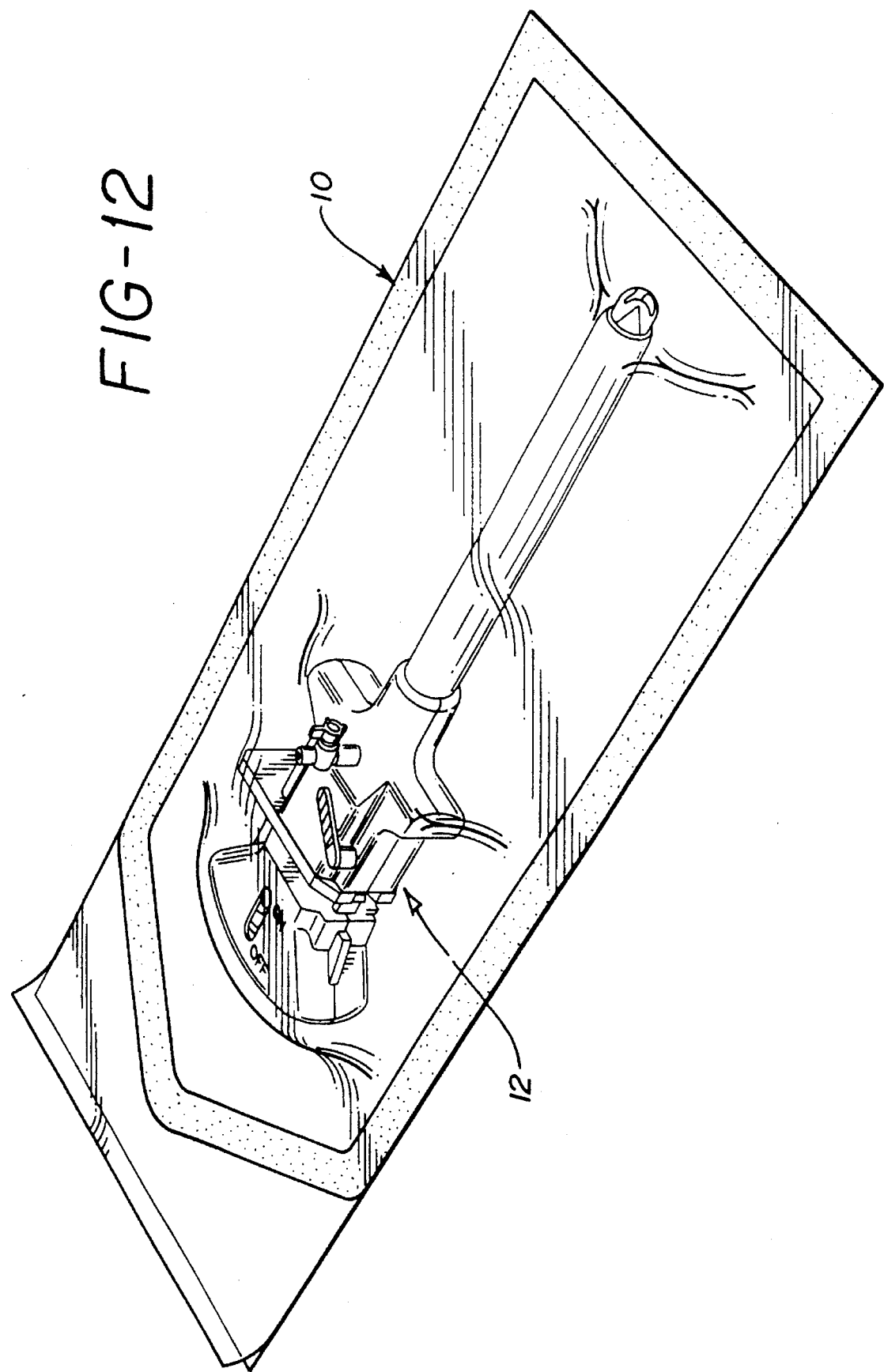

5,562,611

SAFETY INTERPOSER FOR SURGICAL INSTRUMENTS

This is a continuation in part of U.S. application Ser. No. 08/061,973 filed on May 17, 1993, now abandoned.

FIELD OF THE INVENTION

This invention relates to packaging for use in transportation, handling and storage of surgical instruments including a means to prevent engagement of the surgical instrument or movement of a safety means from a safety position where upon engagement or movement of the instrument, sharp edges or points of the instrument could be exposed.

BACKGROUND OF THE INVENTION

It is important for surgical instruments to be packaged in a readily presentable sterile condition. If the instrument is engaged, particularly if the instrument has sharp edges exposable when engaged, it may disturb the packaging containing the instrument so as to compromise its sterile environment. For example, if a tip of a trocar or an insufflation needle is exposed, it may puncture the packaging.

Flexible packaging is particularly vulnerable to such puncturing or disturbance. Flexible packaging is defined herein as a packaging which does not rigidly conform to the contents of the package. Examples of such packaging are surgical drapes and closed cell foam which may be formed from materials such as, for example, cellulose or plastics. The use of flexible packaging has become increasingly desirable as opposed to thermoformed blister packaging or styrofoam type packaging which have recently become less desirable for reasons relating to economics, ease of packaging disposal in the operating room, processing considerations and environmental concerns.

It is therefore desirable in the sterile packaging of surgical instruments, especially flexible packaging, to prevent unintended engagement of the device or movement of a safety mechanism from its safety position, which could expose a sharp instrument.

A trocar assembly for use in endoscopic surgical procedures generally comprises two major components, an obturator and a cannula. The obturator is initially positioned within the cannula and has a puncturing or penetrating tip which typically extends from the cannula. The obturator tip is used to penetrate the skin and underlying tissue to provide cannula access to a body cavity. The obturator may then be removed and laparoscopic or arthroscopic surgery performed through the cannula. An example of such a device is described in U.S. Pat. No. 4,535,773.

Typically, in transportation and storage as well as in use, the obturator is positioned in the cannula and the puncturing or penetrating tip of the obturator extends from the distal end of the cannula. However, many trocars have safety shields which cover the tip of the obturator. If the trocar is not armed, the safety shield is maintained in its tip covering position. When the trocar assembly is engaged for puncturing, the safety shield can be moved to expose the puncturing or penetrating tip of the obturator.

An example of a means for engagement of the trocar is a safety spring which is actuated by a spring actuating element connected to the distal end of an obturator handle. When the obturator is inserted into the cannula, a portion of the spring actuating element located at the distal end of the obturator handle engageably interacts with the proximal end of a cannula handle to move the safety spring from a first position to a second position. In the second position, the safety shield can then be retracted from its covering position over the obturator tip. An example of such a safety spring is described in U.S. Pat. No. 5,114,407.

It is therefore desirable in the packaging of trocar assemblies to prevent unintended engagement.

A Verress-type or insufflation needle typically comprises a sharp needle having a lumen extending therethrough. An inner needle having a rounded safety tip extends through the lumen and distally beyond the sharp distal needle tip. When the safety tip engages with an outside object, if the force is great enough, the safety tip moves axially and proximally within the needle to expose the sharp needle tip. An example of such a needle is described in U.S. Pat. No. 5,139,485.

It is therefore desirable when packaging a Verress needle to prevent proximal axial movement of the safety tip away from its safety position.

It is also desirable to prevent unintended engagement of surgical instruments to avoid other safety concerns which may be posed by an exposed sharp instruments.

SUMMARY OF THE INVENTION

The present invention provides an interposer means to prevent engagement of a surgical instrument or a corresponding movement of a safety mechanism, to expose a sharp instrument such as a cutting or puncturing instrument, e.g., a trocar tip. More particularly, the present invention provides a safety interposer which may be used for packaging surgical instruments in a sterile packaging environment. The safety interposer acts to prevent coupling or engagement of interactive parts of the instrument or prevent movement of a safety mechanism from a safety position.

In a preferred embodiment of the present invention, a safety interposer is used to prevent coupling of a cannula handle and an obturator handle of a trocar assembly where such coupling acts to engage the trocar assembly. The interposer thereby prevents the trocar obturator from inadvertently extending from its safety shield.

Another feature of the present invention provides a safety interposer with a slotted hole configuration to allow it to fit around the shaft or tubular member of an instrument and to be easily removed by pulling it in a direction approximately perpendicular to the instrument's axis.

In a preferred embodiment of the invention, the safety interposer is shaped to fit around the shaft of the obturator and act as a physical barrier to prevent a spring actuating element located on the distal end of the obturator handle, engaging the cannula handle to thereby permit movement of the safety shield.

In another embodiment a safety interposer may be inserted around the shaft of an inner needle with a safety tip which is inserted into a hollow insufflation needle, to prevent depression of the safety tip to expose the sharp hollow outer needle. A notch is cut through the hollow needle or its housing and into the inner needle. The shaft of the inner needle is adapted to receive the interposer to physically block the tip's longitudinal axial movement with respect to the hollow needle, thereby avoiding exposing the sharp hollow needle tip. The safety interposer may also be shaped to fit around a tubular member attached to the inner needle with safety tip. The safety interposer is physically removable from the instrument.

DETAILED DESCRIPTION OF THE DRAWINGS

FIG. 1 illustrates a perspective view of an uncoupled trocar assembly with a safety interposer.

FIG. 2 illustrates an exploded perspective view of an uncoupled trocar assembly with a safety interposer.

FIG. 3 illustrates a perspective view of a coupled trocar assembly with the safety mechanism covering the obturator.

FIG. 4 illustrates a partial perspective view of an exposed obturator tip with a retracted safety mechanism.

FIG. 5 illustrates a partial cross sectional view of a trocar assembly with a safety interposer taken along lines 5—5 of FIG. 1.

FIG. 6 illustrates an cross sectional view of a trocar assembly of FIG. 3 with parts broken away.

FIG. 7 illustrates a bottom plan view of a safety interposer with a trocar assembly.

FIG. 8 illustrates a safety interposer of the present invention as seen along line 8—8 of FIG. 7.

FIG. 9 illustrates a cross-section of a Verress-type needle with a safety interposer.

FIG. 10 illustrates a cross section of the Veress-type needle illustrated in FIG. 9 along line 10—10.

FIG. 11 illustrates a cross section of the Veress-type needle illustrated in FIG. 9 along line 11—11.

FIG. 12 illustrates a perspective view of the trocar assembly contained in a flexible sterile outer wrap 10.

DETAILED DESCRIPTION OF THE PREFERRED EMBODIMENT

Referring now to FIGS. 1–8 and 12 there is illustrated a trocar assembly 12 comprising a cannula 14 and an obturator 22. FIG. 12 illustrates the trocar assembly contained in a flexible sterile outer wrap 10. The cannula 14 comprises a cannula handle 15 with a proximal end 16. The proximal end 16 of the cannula handle 15 has an outer circumferential rim 17 which projects proximally outward from the proximal end 16 of the cannula handle 15. The obturator 22 comprises an obturator handle 24, an obturator shaft 26, a puncturing tip 23 and a safety shield 25. The obturator handle 24 comprises a distal end 28 which has coupling means 27 and a safety mechanism 30 comprising a spring actuator 31 and a safety spring 32.

The coupling means 27 may be received by the proximal end 16 of the cannula handle 15 to couple the obturator 22 with the cannula 14. In coupling with the cannula 14, the coupling means 27 extend inside and beyond the rim 17 of the cannula handle 15 towards the end 16.

The safety mechanism 30 is shown in a safety position in FIGS. 1, 2, 5, 7 and 8 and in its released or engaged position in FIGS. 3, 4 and 6 which illustrate a coupled trocar assembly 12. When the trocar assembly 12 is coupled, the rim 17 of the cannula handle proximal end 16 contacts and depresses the spring actuator 31. The depressed spring actuator 31 causes the safety spring 32 to move to release the safety shield 25. A mechanism by which a similar spring actuator operates to release a safety shield is described in U.S. Pat. No. 5,114,407 incorporated herein by reference.

Referring now to FIGS. 2 and 8, there is illustrated a safety interposer 40 having a first and a second arm 41 and 42 defining a slot, relatively circular in shape. Each of the first and second arm 41 and 42 has an inwardly projecting element 43 which serves to narrow the slot and close the circle to permit the safety interposer 40 to engage relatively snugly around the obturator shaft 26 (FIG. 8) while not closing completely around the shaft. The slot permits the interposer 40 to be inserted around the shaft 26 and removed when a pulling force, generally perpendicular to the trocar axis, is applied to the interposer 40 on a side 44 opposite the slot. The side 44 projects from the trocar assembly 12 so that a user may grasp the side 44 to remove the interposer 40 from the trocar assembly 12.

The interposer 40 is of sufficient length and width so that when it is inserted between the cannula handle proximal end 16 and obturator handle distal end 24, it contacts the outer circumferential rim 17 extending from cannula handle proximal end 16. The interposer 40 is sufficiently rigid so that it will not displace distally from the rim 17 towards the cannula proximal end 16 to an extent that the rim 17 can depress the spring actuator 31 and engage the safety mechanism 30. Thus the interposer 40 prevents engagement of the trocar.

FIGS. 1, 5 and 7 illustrate a trocar assembly 12 with a safety interposer 40 inserted between the cannula handle 15 and the obturator handle 24. The obturator coupling means 27 extend further distally from the obturator handle 24 than the spring actuator 31. Therefore when the interposer 40 is positioned between the distal end 28 of the obturator handle 20, and the proximal end 16 of the cannula handle, the interposer 40 blocks the coupling means 27 from coupling the obturator 22 with the cannula 14. Because the coupling means 27 extend a greater distance from the distal end 28 of the obturator, the interposer 40 does not come in contact with the spring actuator 31. Thus the interposer 40 creates a physical barrier to prevent depression of the spring actuator 31 which when depressed, releases the safety spring 32 and permit the safety shield 25 to be moved from a protective safety position covering the puncturing tip 23 of the obturator 22 as illustrated in FIGS. 3, 4 and 6.

Referring now to FIGS. 9–11 there is illustrated a Veress-type needle 100 with a safety interposer 140 similar to interposer 40 illustrated in FIGS. 1–8. The interposer 140 includes a first and second arm 141, 142 and a side or an end 144, together which define a slot. The arms 141, 142 are adapted to be inserted around the shaft of the Veress-type needle 100 as set forth below. The end 144 may include a grasping surface for grasping and removing the safety interposer 140 from the instrument.

The Veress needle 100 has an outer needle 101 with a sharp tip 112. The outer needle 101 is maintained in a housing 102 having inserted in it, an inner needle 104 with a rounded or blunt tip 105. The inner needle 104 is spring loaded at the end 109 of a spring 107. Without the interposer 140, the tip 112 may be depressed and cause the inner needle 104 to retract into the handle 102, the needle 104 moving axially with respect to the needle 101 thereby exposing the sharp tip 112. Use of a similar Veress-type needle is more fully described in U.S. Pat. No. 5,139,485 incorporated herein by reference.

The interposer is inserted through a slot 120 cut partially through opposite sides of the width of the housing 102, through a circumferential portion of the needle 101, and into the inner needle 104. The slot 120 is adapted to receive the interposer 140 which then physically blocks the inner needle's longitudinal axial movement with respect to the hollow needle 101 and thereby avoid exposing the sharp hollow needle tip 112. The safety interposer 140 is physically removable from the instrument. The safety interposer 140 may also be shaped to fit around a tubular member 108 attached to the inner needle (this embodiment is not illustrated).

Although the above description refers to specific uses of the safety interposer with a trocar assembly or an insufflation or Veress-type needle, it is not intended to be limited to the specific embodiment described. For example the interposer may be used with any surgical cutting instrument which has a shaft or tubular member around which the interposer may fit such that the interposer acts as a physical barrier to prevent movement of a safety means from a safety position whereby a sharp edge or point could be exposed or where the interposer acts to prevent engagement of two interactive parts which if engaged would permit exposure of a sharp edge or point.

It may be observed from the above that numerous equivalents or modifications may be made without departing from the spirit and scope of the invention. No limitation to the claimed invention is intended from the specific embodiments described herein.

What is claimed is:

1. In combination, a surgical instrument and a safety device for use therewith comprising:

a surgical instrument comprising:

a shaft comprising an outer needle, wherein said shaft has a proximal end and a distal end, a handle coupled to the proximal end of the shaft, a tissue treating portion coupled to the distal end of said shaft, and a safety mechanism comprising an inner needle, said inner needle having a blunt tip and being disposed within said outer needle, said tissue treating portion comprising a sharp tip on said outer needle; and a safety device comprising a safety interposer having a slot adapted to at least partially receive said shaft of said surgical instrument, wherein said slot has a shape that permits the interposer to fit at least partially around the shaft, and wherein the safety interposer is adapted to act as a physical barrier to prevent movement of said safety mechanism of the surgical instrument from a safety position wherein said safety position is where the tip of the inner needle extends beyond the sharp tip of the outer needle.

2. The safety device of claim 1 wherein:

said safety needle comprises a notch; and said slot of said interposer is shaped to fit in the notch to prevent said tip of said inner needle from retracting within the outer needle to expose the sharp tip.

* * * * *